US011219779B2

(12) United States Patent
Crepin et al.

(10) Patent No.: US 11,219,779 B2
(45) Date of Patent: Jan. 11, 2022

(54) DEVICE FOR GENERATING A VERY-LOW-FREQUENCY PULSED MAGNETIC FIELD CARRIED BY A VERY-LOW-FREQUENCY ALTERNATING MAGNETIC FIELD

(71) Applicant: G.C. TECHNOLOGY, Aix en Provence (FR)

(72) Inventors: Gérard Crepin, Aix en Provence (FR); Pascal Rudent, Auriol (FR)

(73) Assignee: G.C. TECHNOLOGY, Aix En (FR)

( * ) Notice: Subject to any disclaimer, the term of this patent is extended or adjusted under 35 U.S.C. 154(b) by 0 days.

(21) Appl. No.: 17/055,861

(22) PCT Filed: May 15, 2019

(86) PCT No.: PCT/FR2019/051109
§ 371 (c)(1),
(2) Date: Nov. 16, 2020

(87) PCT Pub. No.: WO2019/220060
PCT Pub. Date: Nov. 21, 2019

(65) Prior Publication Data
US 2021/0220664 A1 Jul. 22, 2021

(30) Foreign Application Priority Data
May 18, 2018 (FR) ...................................... 1854157

(51) Int. Cl.
*A61N 2/12* (2006.01)
*A61N 2/00* (2006.01)

(52) U.S. Cl.
CPC ................ *A61N 2/12* (2013.01); *A61N 2/008* (2013.01)

(58) Field of Classification Search
CPC . A61N 2/00; A61N 2/004; A61N 2/02; A61N 2/06; A61N 2/12
(Continued)

(56) References Cited

U.S. PATENT DOCUMENTS 4,537,181 A * 8/1985 Shalhoob ................. A61N 2/12
600/9
5,667,469 A * 9/1997 Zhang ...................... A61N 2/12
600/9
(Continued)

FOREIGN PATENT DOCUMENTS

DE 202017003178 U1 7/2017
EP 1364679 A2 11/2003
(Continued)

OTHER PUBLICATIONS

International Search Report and Written Opinion from PCT Application No. PCT/FR2019/051109, dated Aug. 23, 2019.
(Continued)

*Primary Examiner* — Samuel G Gilbert
(74) *Attorney, Agent, or Firm* — Workman Nydegger

(57) ABSTRACT

The invention relates to a device for generating a very-low-frequency pulsed magnetic field carried by a very-low-frequency alternating magnetic field and intended to be applied to a region of the human body, the device is provided with a plurality of pairs of angular magnet sectors of opposite polarity, the pairs of angular magnet sectors being centered on one same axis of rotation, angularly spaced apart from one another, and set in rotation at a predetermined speed about the axis of rotation so as to generate an alternating magnetic field at a predefined frequency, and at least one conductive wire coil centered on the axis of rotation of the angular magnet sectors and supplied with a pulsed electric current so as to generate a pulsed magnetic field superimposed over the alternating magnetic field gen-
(Continued)

erated by the setting in rotation of the angular magnet sectors.

10 Claims, 4 Drawing Sheets

(58) Field of Classification Search
USPC ........................................................ 600/9–15
See application file for complete search history.

(56) References Cited

U.S. PATENT DOCUMENTS

| | | |
|---|---|---|
| 5,935,054 A | 8/1999 | Loos |
| 2018/0078780 A1 | 3/2018 | Sun et al. |

FOREIGN PATENT DOCUMENTS

| | | | |
|---|---|---|---|
| FR | 3073148 A1 | 5/2019 | |
| WO | 2008014902 A1 | 2/2008 | |

OTHER PUBLICATIONS

Search Report from corresponding FR Application No. FR1854157, dated Feb. 7, 2019.
Funk et al., "Potent Stimulation of Blood Flow in Fingers of Volunteers after Local Short-Term Treatment with Low-Frequency Magnetic Fields from a Novel Device", Evidence-Based Complementary and Alternative Medicine, vol. 2014, Article ID 543564, Hindawi Publishing Corporation, May 21, 2014, 9 pages.

\* cited by examiner

DEVICE FOR GENERATING A VERY-LOW-FREQUENCY PULSED MAGNETIC FIELD CARRIED BY A VERY-LOW-FREQUENCY ALTERNATING MAGNETIC FIELD

FIELD

Background of the Invention

The present invention relates to the general field of magnetotherapy, and in particular to devices generating an induced, low-frequency, sinusoidal electric current intended to be applied to a region of the human body for the purpose of producing analgesic and anti-inflammatory action.

As is known, to generate an induced electric current, magnetotherapy uses a variable magnetic field in particular to relieve joint pain and peripheral joint pain, this variable magnetic field being created by a magnetic source, a coil or magnet. For magnets, these are set in movement to create the induced current Magnetic fields also have an impact on microcirculation which regulates blood flow at the periphery of the body (limbs) but also at different organs. As shown by a study by Funk in 2014, exposure for 5 minutes to a sinusoidal magnetic field of 10 to 15 mT varying between frequencies of 4 to 12 Hz, increases hand microcirculation in healthy subjects. In a population of young, type 1 diabetics having the characteristic microcirculation insufficiency of their pathology, a study by Nikolaeva et al in 2008 also shows a strong increase in skin microcirculation in the leg after exposure for 15 minutes to a sinusoidal magnetic field of 45 mT to 16 Hz, compared with a group exposed to a placebo device.

Magnetotherapy can be implemented using a device (usually portable device) moved over a region of the body to be treated, this device containing magnets e.g. rotating magnets and a motor to enable these magnets to generate a variable magnetic field inducing an electrical field proportional to the rate of change (Faraday's law).

From document WO 2008/014902 a portable device is known to generate a sinusoidal magnetic field for therapeutic purposes, this device comprising four angular magnet sectors that are flat, of same geometric shape, centred on one same axis of rotation and angularly spaced apart from one another, two adjacent angular magnet sectors having opposite polarity. Thus arranged, the angular magnet sectors are driven in rotation by a motor to generate a sinusoidal magnetic field at a predefined frequency.

It is also known that the therapeutic effect obtained is related to the electric currents induced by rotation of the angular magnet sectors, provided that the intensity of these currents exceeds a certain threshold. It is additionally known that induced currents are proportional to the speed of linear movement of the magnets. However, for a given speed of rotation, the speed of linear movement is greater at the end part of the angular magnet sectors than at their axis of rotation. In addition, to obtain a sinusoidal magnetic field with the device described in document WO 2008/014902, it is necessary to use magnets in the form of angular sectors, which further reduces the magnetic field at the centre of the device.

Therefore, the device described in document WO 2008/014902 has the disadvantage that the intensity of the induced electric currents at the centre of the device does not exceed the threshold needed to obtain a therapeutic effect. Yet, the centre of the device is typically the area on which most demand is placed by a user of the device. A user will naturally tend to centre the device on the pain or pathology to be treated.

A further disadvantage of the device described in this document is that the space between the magnets generates a dual peak signal in a zone close to the surface of the device, and hence major harmonic distortion.

Additionally, since the therapeutic effects of said devices are obtained at very low frequencies, preferably lower than 10 Hz, it is not desirable to increase the field $\vec{V} \times \vec{B}$ by increasing the speed of rotation of the magnets. The consequence of this increase in the field $\vec{V} \times \vec{B}$ would be a reduction in the therapeutic effects obtained.

OBJECT AND SUMMARY OF THE INVENTION

The objective of the present invention is therefore to propose a device intended for magnetotherapy which does not have the aforementioned disadvantages.

According to the invention, this objective is reached with a device for generating a very-low-frequency, pulsed magnetic field carried by a very-low-frequency alternating magnetic field and intended to be applied to a region of the human body, the device comprising:
a plurality of pairs of angular magnet sectors of opposite polarity, the pairs of angular magnet sectors being centred on one same axis of rotation, angularly spaced apart from one another, and set in rotation at a predetermined speed about the axis of rotation so as to generate an alternating magnetic field at a predefined frequency; and
at least one conductive wire coil centred on the axis of rotation of the angular magnet sectors and supplied with a pulsed electric current so as to generate a pulsed magnetic field superimposed over the alternating magnetic field generated by the setting in rotation of the angular magnet sectors.

The conductive wire coil centred on the axis of rotation of the angular magnet sectors and supplied with a pulsed electric current creates a strong, induced electric current in the centre of the zone of action of the device, which allows offsetting of the non-homogeneity of the current induced by the rotating angular magnet sectors. Also, the conductive wire coil has little effect on the periphery of the angular magnet sectors (contrary to the latter) which means that the association of these two elements allows a strong, induced electric current to be obtained at every point of the zone of action of the device. Therefore, the intensity of the induced electric current lies above a predefined threshold between the axis of rotation and the free end of the angular magnet sectors.

In addition, the inventors have ascertained that the generation of a low-frequency, pulsed magnetic field carried by an alternating magnetic field increases blood microcirculation in the region of the human body to which the device is applied. In particular, measurements unexpectedly show a significantly greater increase in blood microcirculation than with the sole setting in rotation of the angular magnet sectors or sole powering of the conductive wire coil. The result of these measurements evidences that the effect in terms of blood microcirculation is greater than the sum of the effects of each of the two fields.

As a result, the generation by the device of the invention of a sudden variation in magnetic field by supplying the conductive wire coil with a pulsed electric current allows the creation of an induced voltage having major analgesic and anti-inflammatory effects.

Preferably, the conductive wire coil is supplied with a pulsed electric current in the form of regular pulses of 1 ms duration and frequency of 20 Hz, generating an intensity allowing the generation of a magnetic field of 1 to 2 mT. The conductive wire coil of very narrow diameter allows a strong, induced current to be obtained despite the weak magnetic current and with low energy consumption. The system thus formed only scarcely modifies the maximum value of the magnetic field and can be portable and self-sufficient.

Also preferably, the device further comprises means to cause the pulse frequency of the pulsed electric current to vary during a cycle of use. With this characteristic, it is possible to modify the frequency spectrum to suit different pathologies via a better adapted signal.

Also preferably, the device further comprises means to cause the rotation frequency of the pairs of magnet sectors to vary during a cycle of use. Therefore, the generated sinusoidal signal moves through different frequencies each of which has proved to be efficient.

The rotation frequency of the pairs of magnet sectors is advantageously less than or equal to 10 Hz.

The conductive wire coil can be a circular coil centred on the axis of rotation of the angular magnet sectors. The conductive wire coil can be a figure-of-eight coil allowing maximization of the effect at a specific point (so-called «butterfly» coils).

Further preferably, each angular magnet sector has one same geometric shape with an inner angular opening of 90° at the axis of rotation, an outer angular opening of between 20° and 50° at a free end opposite the axis of rotation, and two side edges defining a radius extending over a distance of between one third and two thirds of a distance separating the axis of rotation from the free end of the angular magnet sectors. This particular shape of the angular magnet sectors allows a sinusoidal magnetic field to be obtained having homogeneous intensity above a predefined threshold between the axis of rotation and the free end of the angular magnet sectors.

The device can further comprise a magnetic circuit layer arranged on the back of the pairs of angular magnet sectors. The device can also comprise a magnetic shielding layer arranged around the pairs of angular magnet sectors.

BRIEF DESCRIPTION OF THE DRAWINGS

Other characteristics and advantages of the present invention will become apparent from the description given below, with reference to the appended drawings illustrating an example of embodiment that is in no way limiting. In the Figures.

DETAILED DESCRIPTION OF THE INVENTION

Figure 1:
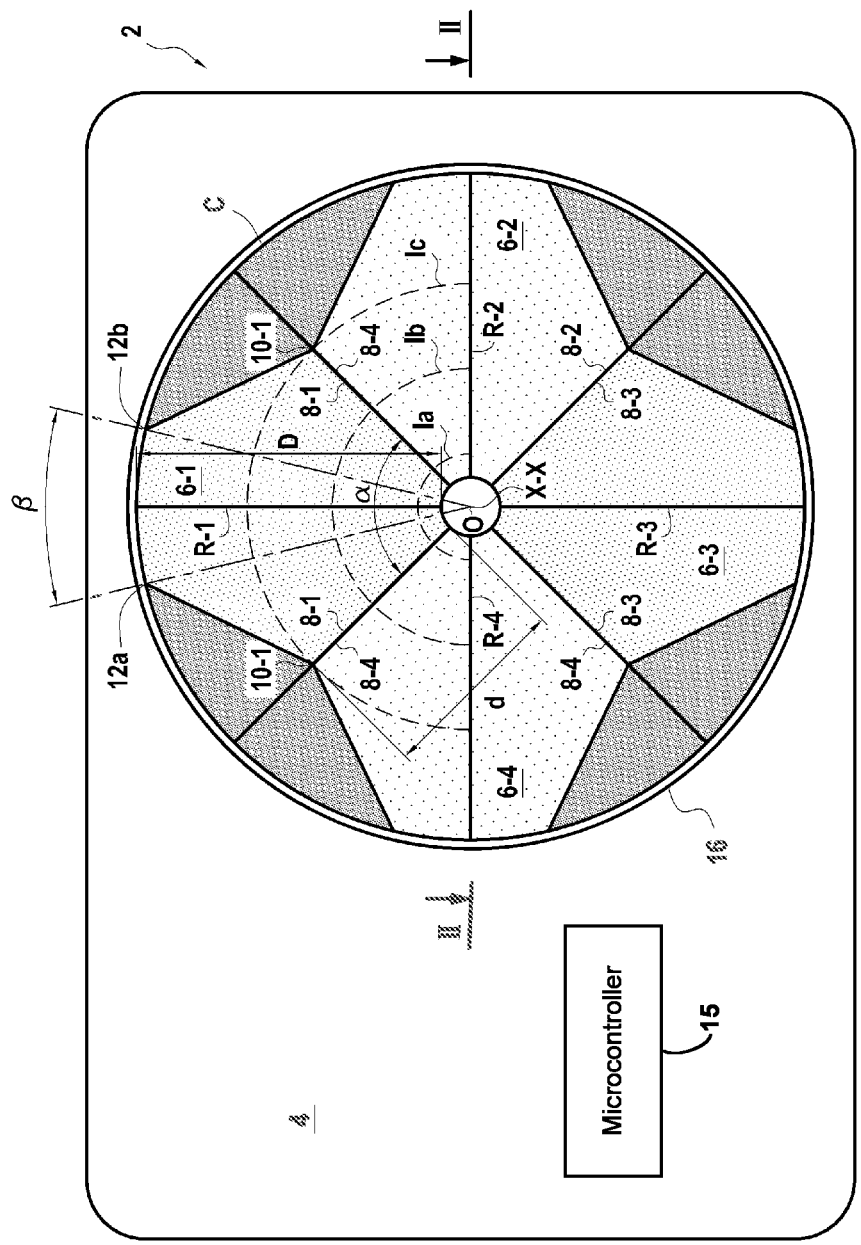
FIG. 1 is a schematic view of a device according to one embodiment of the invention.
Figure 2:
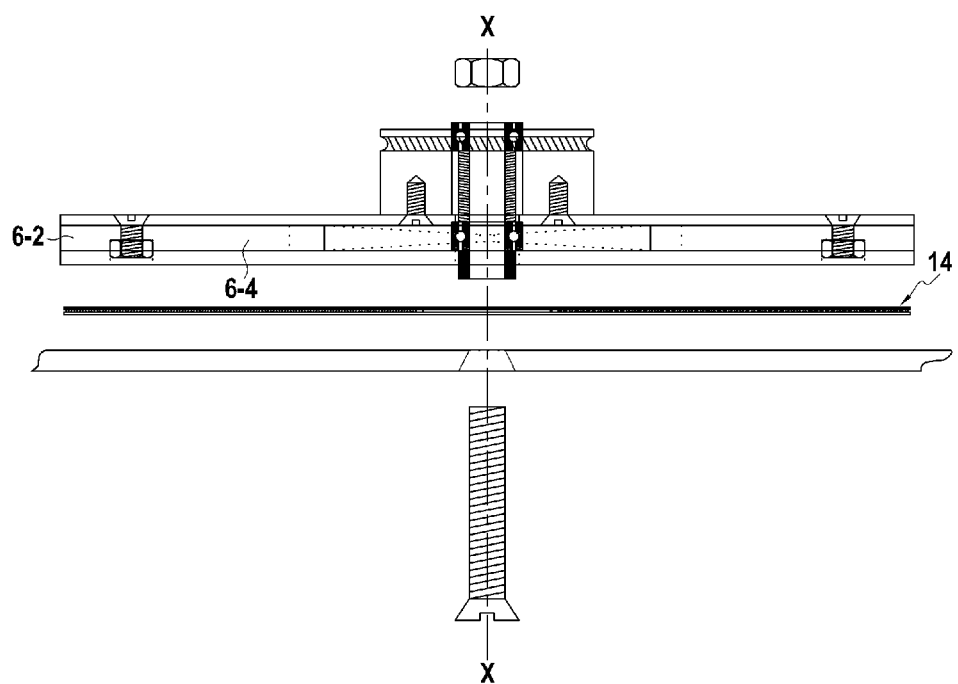
FIG. 2 is a cross-sectional view along II-II in FIG. 1.

FIGS. 1 and 2 schematically illustrate a portable device 2 of the invention to generate a low-frequency pulsed magnetic field carried by an alternating magnetic field, and intended to be applied to a region of the human body.

This device 2 comprises a casing 4 inside which there are assembled two pairs of angular magnet sectors 6-1 to 6-4 as described in patent application FR 17 60443 filed by the Applicant.

As described in this patent application FR 17 60443, the angular magnet sectors 6-1 to 6-4 have one same geometric shape, are centred on one same axis of rotation X-X, and are contained within a circle C of diameter D and centre O.

More specifically, the angular magnet sectors 6-1 to 6-4 are angularly spaced apart from one another about the axis of rotation X-X and are arranged so that two adjacent angular magnet sectors have opposite polarity (North or South).

The device 2 also comprise means to set the pairs of angular magnet sectors in rotation about the axis of rotation X-X. In one embodiment, these means are in the form of an electric motor and belt transmission. Evidently any other means could be envisaged to ensure this setting in rotation.

Preferably, the four angular magnet sectors 6-1 to 6-4 are each of symmetrical shape relative to a radius of symmetry, R-1 to R-4 respectively, of the circle C within which they are contained.

Each angular magnet sector 6-1 to 6-4 comprises two side edges 8-1 to 8-4 which are symmetrical relative to the radius of symmetry of the angular magnet sector and they face or are in direct contact with the corresponding side edges of two adjacent angular magnet sectors.

In addition, the two side edges 8-1 to 8-4 of each angular magnet sector define a joining radius (delimited between the centre O of circle C and point 10-1 to 10-4 of the side edge the furthest distant from the centre O) which extends over a distanced corresponding to two thirds of the radius D/2 of circle C (i.e. two thirds of the distance separating the axis of rotation X-X from the free end of the angular magnet sectors). For practicality reasons, only points 10-1 of the angular magnet sector 6-1 are shown in FIG. 1.

In addition, the side edges 8-1 to 8-4 of each angular magnet sector together form an angle α of 90° (it can also be said that the inner angular opening α of each angular magnet sector at the axis of rotation X-X is 90°).

Also preferably, each angular magnet sector further comprises an outer angular opening β at a free end opposite the axis of rotation X-X which is between 20° and 50°, and is preferably 45°.

In other words, the free end of each angular magnet sector 6-1 to 6-4 is preferably delimited between two points 12a, 12b positioned on circle C within which the angular magnet sectors are contained. These points are symmetrical and the radii formed by points O and 12a, and by O and 12b, together form an angle β of between 20° and 50°, and preferably of 45°.

The angular magnet sectors 6-1 to 6-4 of the device of the invention are set in rotation about the axis of rotation X-X preferably at a speed of 300 rpm, which generates an induced sinusoidal electric current at a frequency preferably lower than or equal to 10 Hz. This setting in rotation of the angular magnet sectors 6-1 to 6-4 of the device generates an alternating magnetic field.

As illustrated in FIG. 2, the device 2 of the invention further comprises at least one conductive wire coil 14 centred on the axis of rotation X-X of the angular magnet sectors and supplied with a pulsed electric current.

This coil 14 is for example a circular coil centred on the axis of rotation of the angular magnet sectors. It can be made of copper wire having a diameter of less than 0.5 mm, with a single layer of turns, the outer diameter thereof covering the outer diameter of the magnets.

Also, this coil is supplied with pulsed electric voltage. By «pulsed electric voltage» it is meant a variation in electric voltage in the form of regular, uniform pulses over time, of which the pulse duration (or generation time) and pulse recurrence time (or frequency) can be determined. They may also be irregular pulses that are known however and known how to reproduce.

Preferably, the pulsed electric voltage supplying the conductive wire coil 14 is in the form of regular pulses of less than 1 ms duration, frequency of 20 Hz and generating sufficient intensity to generate a maximum magnetic field of 1 to 2 mT.

In this manner, the conductive wire coil 14 generates a pulsed magnetic field superimposed over the alternating magnetic field generated by the setting in rotation of the angular magnet sectors 6-1 to 6-4.

It will be noted that the conductive wire coil can be a figure-of-eight coil («butterfly» type coil) centred on the axis of rotation X-X of the angular magnet sectors.

It will also be noted that the device 2 of the invention may further comprise means (of microcontroller type 15) to cause the pulse frequency of the pulsed electric current supplying the conductive wire coil 14 and/or the rotation frequency of the pairs of magnet sectors 6-1 to 6-4 to vary during a cycle of use.

This characteristic is particularly advantageous for varying the magnetic field generated by the device during a cycle of use.

It will be further noted that the angular magnet sectors 6-1 to 6-4 are driven in rotation about the axis of rotation X-X by an electric motor (not illustrated) independent of the electric supply to the coil 14. Also, when the coil 14 is powered the polarity thereof remains unchanged. In particular, the coil does not undergo any polarity reversal when the device of the invention is in operation.

Figure 3A:
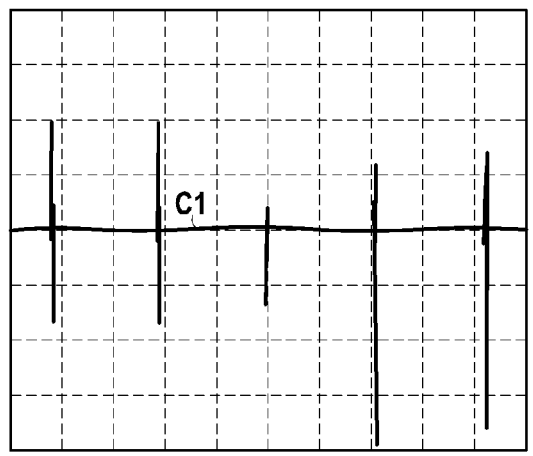
FIGS. 3A and 3B are examples of pulsed magnetic fields generated by the device of the invention.
Figure 3B:
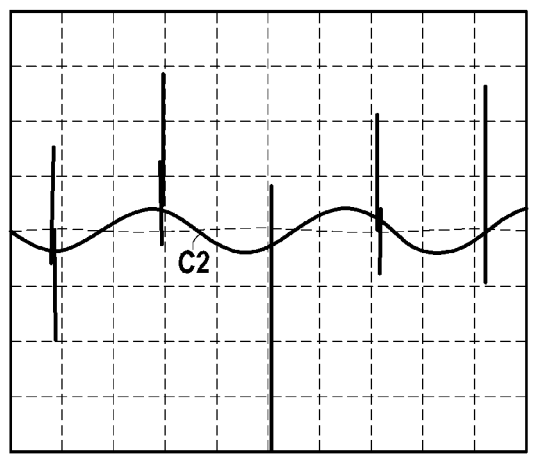

FIGS. 3A and 3B illustrate examples of a magnetic field (as a function of time) generated by superimposition of these two fields.

In particular, FIG. 3A gives an example of a curve showing the induced current C1 generated by the device of the invention in the centre thereof i.e. at the axis of rotation X-X of the angular magnet sectors. FIG. 3B gives an example of a curve showing the alternating induced current C2 at a distance of one centimetre from the centre of the device.

These two curves of induced current C1, C2 clearly show each of the pulses carried by a sine wave. In particular, it is ascertained that the intensity of the pulses carried by the sine-wave is greater in the centre of the device and decreases on moving away from the centre. Therefore, the conductive wire coil when supplied with pulsed electric current creates a strong induced current at the centre of the device and of lesser intensity on the periphery thereof.

Figure 4:
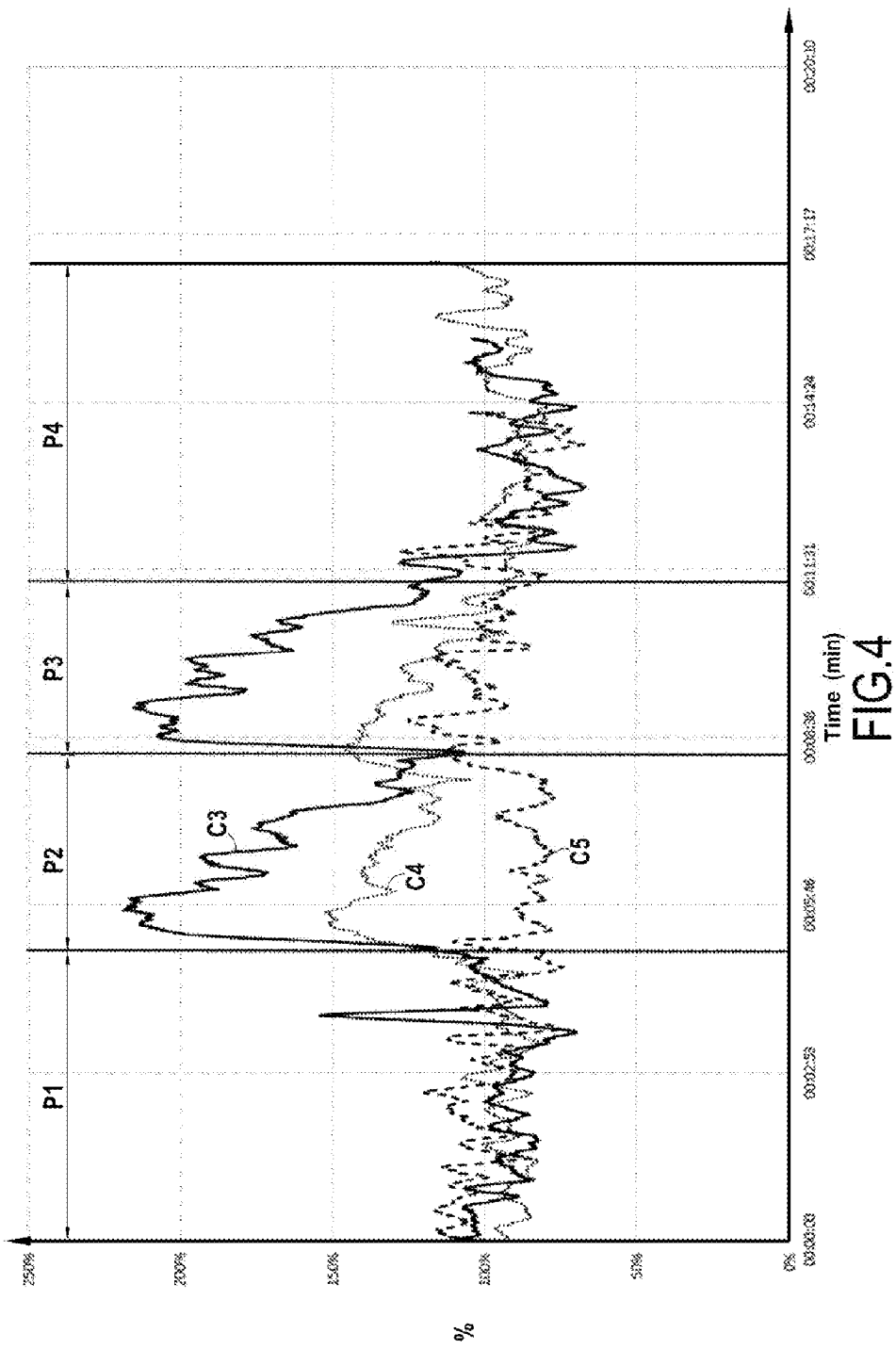
FIG. 4 gives curves showing the blood microcirculation obtained with the device of the invention, with a device having rotating magnets, and with a device having a conductive wire coil.

FIG. 4 illustrates a test example of the device of the invention and the results obtained on blood microcirculation in a region of the human body exposed to the device over several cycles of application.

More specifically, the test of the device was conducted on a person's hand with the following operating mode: a rest period P1 (lasting 5 mn), a first cycle of application of the device P2 (lasting 3 mn), a second cycle of application of the device P3 (lasting 3 mn), and a period of return to normal P4 (lasting 15 mn).

Using a blood perfusion imaging system, it was possible directly to measure the level of skin perfusion (i.e. blood microcirculation) throughout the test. The data given by the imager were normalised in relation to the mean of the values of the last minute of the rest period P1 to express the percentage increase in microcirculation during the test.

FIG. 4 gives three different curves corresponding to three different tests: a curve C3 corresponding to a test using a device of the invention; a curve C4 corresponding to a test using a magnetotherapy device having a conductive wire coil but without rotating magnets, and a curve C5 corresponding to a test using a device having rotating magnets but without a conductive wire coil.

It is ascertained that the effect on blood microcirculation obtained by applying the device of the invention during the application cycles P2, P3 (curve C3) is largely greater than the simple addition of the effects obtained with the two other devices (curves C4 and C5). An increase of 100% is found in global blood perfusion of the hand at the start of the two application cycles P2, P3, whereas this increase is only 50% for the device without conductive wire coil (curve C5). For the device without rotating magnets (curve 4) there is very little effect on microcirculation.

In addition, as for the device described in patent application FR 17 60443, it will be noted that the device of the invention can have angular magnet sectors of varying thicknesses and can be provided with a magnetic circuit layer arranged on the back of the pairs of angular magnet sectors and with a magnetic shielding layer arranged around the pairs of magnetic angular sectors (not illustrated in the Figures). In this case, the antenna is positioned on the side opposite the magnetic circuit so that the magnetic field of the circular antenna is not attenuated by the magnetic circuit.

The invention claimed is:

1. A device for generating a very-low-frequency, pulsed magnetic field carried by a very-low-frequency alternating magnetic field, and intended to be applied to a region of a human body, the device comprising:
    a plurality of pairs of angular magnet sectors of opposite polarity, the pairs of angular magnet sectors being centered on one same axis of rotation, angularly spaced apart from one another, and set in rotation at a predetermined speed about the axis of rotation so as to generate an alternating magnetic field at a predefined frequency; and
    at least one conductive wire coil centered on the axis of rotation of the angular magnet sectors and supplied with a pulsed electric current so as to generate a pulsed magnetic field superimposed over the alternating magnetic field generated by the setting in rotation of the angular magnet sectors.

2. The device according to claim 1, wherein the conductive wire coil is supplied with a pulsed electric voltage in a form of regular pulses of less than 1 ms duration, frequency of 20 Hz and generating sufficient intensity to generate a magnetic field of 1 to 2 mT.

3. The device according to claim 2, further comprising a microcontroller to cause the pulse frequency of the pulsed electric current to vary during a cycle of use.

4. The device according to claim 1, further comprising a microcontroller to cause a rotation frequency of the pairs of magnet sectors to vary during a cycle of use.

5. The device according to claim 1, wherein a rotation frequency of the pairs of magnet sectors is less than or equal to 10 Hz.

6. The device according to claim 1, wherein the conductive wire coil is a circular coil centered on the axis of rotation of the angular magnet sectors.

7. The device according to claim 1, wherein the conductive wire coil is a figure-of-eight coil.

8. The device according to claim 1, wherein each said angular magnet sector has one same geometric shape with an inner angular opening (α) of 90° at the axis of rotation, an outer angular opening (β) of between 20° and 50° at a free end opposite the axis of rotation, and two side edges defining a radius extending over a distance of between one third and two thirds of a distance separating the axis of rotation from the free end of the angular magnet sectors.

9. The device according to claim 1 further comprising a magnetic circuit layer arranged on a back of the pairs of angular magnet sectors.

10. The device according to claim 1 further comprising a magnetic shielding layer arranged around the pairs of angular magnet sectors.

\* \* \* \* \*